United States Patent [19]

Kortbeek et al.

[11] 4,410,637

[45] Oct. 18, 1983

[54] PROCESS FOR THE PREPARATION OF A HYDROCARBON MIXTURE FROM $H_2$/CO MIXTURES

[75] Inventors: Andras G. T. G. Kortbeek; Emmanuel E. A. Neel; Guy Barre, all of Grand Couronne, France

[73] Assignee: Shell Oil Company, Houston, Tex.

[21] Appl. No.: 314,264

[22] Filed: Oct. 23, 1981

[30] Foreign Application Priority Data

Dec. 15, 1980 [FR] France ............................. 80 26564

[51] Int. Cl.$^3$ ............................................... C07C 1/04
[52] U.S. Cl. ................................... 518/714; 518/713; 518/715; 518/717; 518/719; 518/721; 502/257; 502/410
[58] Field of Search .............. 518/714, 715, 719, 717, 518/721, 713

[56] References Cited

U.S. PATENT DOCUMENTS

| | | | |
|---|---|---|---|
| 2,754,314 | 7/1956 | McGrath | 518/719 X |
| 3,730,694 | 5/1973 | Wunderlich | 518/719 X |
| 3,976,744 | 8/1976 | Granquist | 423/118 |
| 4,269,783 | 8/1981 | Brennan et al. | 518/721 |

FOREIGN PATENT DOCUMENTS

| | | | |
|---|---|---|---|
| 686373 | 1/1953 | United Kingdom . | |
| 2006260 | 5/1979 | United Kingdom | 518/714 |
| 2006819 | 5/1979 | United Kingdom | 518/714 |
| 1555928 | 11/1979 | United Kingdom | 518/721 |

OTHER PUBLICATIONS

Shabtai, Chemica e l'industria, vol. 61, No. 10, Oct. 1979, pp. 734–741.
Barrer, Zeolites and Clay Minerals as Sorbents and Molecule Sieves, (1978) pp. 407–485.

*Primary Examiner*—Howard T. Mars
*Attorney, Agent, or Firm*—John M. Duncan

[57] ABSTRACT

A process for the preparation of a hydrocarbon mixture from a mixture of carbon monoxide and hydrogen, using a catalyst combination containing one or more metal components with catalytic activity for the conversion of an $H_2$/CO mixture into acyclic hydrocarbons, e.g., Ru, Co, Fe, Ni and Cr, and as carrier a laminar compound capable of absorbing metal ions or metal salts by intercalation. Preferably the laminar compound is a laminar crystalline silicate, e.g., magadiite.

6 Claims, No Drawings

PROCESS FOR THE PREPARATION OF A HYDROCARBON MIXTURE FROM H₂/CO MIXTURES

BACKGROUND OF THE INVENTION

The invention relates to a process for the preparation of a hydrocarbon mixture from a mixture of carbon monoxide and hydrogen, using a catalyst combination containing one or more metal components with catalytic activity for the conversion of an $H_2/CO$ mixture into acyclic hydrocarbons and a carrier.

In an investigation by the applicants concerning this process it was found that it has two drawbacks. In the first place, when using space velocities acceptable in actual practice, the conversion of the $H_2/CO$ mixture is unsatisfactory. Further, the process yields a product substantially consisting of hydrocarbons with more than 12 carbon atoms in the molecule and too few hydrocarbons with 5-12 carbon atoms in the molecule.

Further investigation by the Applicant concerning this process has shown that the two above-mentioned drawbacks can be obviated by using a laminar compound, preferably a laminar crystalline silicate as catalyst carrier, i.e., by contacting the feed with a catalyst containing one or more metal components with catalytic activity for the conversion of an $H_2/CO$ mixture into acyclic hydrocarbons, which metal components are preferably chosen from the group formed by Fe, Ni, Co, Cr and Ru, and which component(s) is/are deposited on a laminar compound, preferably a laminar crystalline silicate capable of absorbing metal ions or metal salts by intercalation. In this manner it is not only achieved that, when using space velocities acceptable in actual practice, a very high conversion of the $H_2/CO$ mixture is obtained, but moreover that the reaction product consists substantially of hydrocarbons with 5-12 carbon atoms in the molecule.

SUMMARY OF THE INVENTION

The present application therefore relates to a process for the preparation of a hydrocarbon mixture, in which a mixture of hydrogen and carbon monoxide is contacted with a catalyst combination containing one or more metal components with catalytic activity for the conversion of an $H_2/CO$ mixture into acyclic hydrocarbons and a carrier, characterized in that use is made of a laminar compound, preferably a laminar crystalline silicate, capable of absorbing metal ions or metal salts by intercalation.

DESCRIPTION OF PREFERRED EMBODIMENTS

In the process according to the invention the starting material is an $H_2/CO$ mixture. Such $H_2/CO$ mixtures can very suitably be prepared by steam gasification or partial combustion of a carbon-containing material. Examples of such materials are wood, peat, brown coal, bituminous coal, anthracite, coke, crude mineral oil and fractions thereof as well as tars and oils extracted from tar sand and bituminous shale. The steam gasification or partial combustion is preferably carried out at a temperature of 900°-1600° C. and a pressure of 10-100 bar. In the process according to the invention it is preferred to start from an $H_2/CO$ mixture with an $H_2/CO$ molar ratio of more than 0.25.

The catalyst combinations used in the process according to the invention contain, in addition to metal components with catalytic activity, a laminar compound, preferably a laminar crystalline metal silicate, characterized in that it can absorb metal ions or metal salts by intercalation. As laminar compound graphite may be used. Although in principle the silicates preferably to be used may contain several metals selected from the group formed by aluminum, iron, gallium, rhodium, chromium and scandium, in the process according to the invention it is preferred to use catalysts in which the silicate contains only one of said metals and in particular silicates containing aluminum, iron or gallium as the metal. Particularly suitable silicates for the process according to the invention are to be found among the clay minerals, especially the pandites, smectites and vermiculites, in which intercalation can be effected by ion exchange with suitable metal ions or metal complex ions, such as chromium ions and cobalt ions. Such clay minerals are described in the book "Zeolites and Clay Minerals as Sorbents and Molecular Sieves" by R. M. Barrer (1978), pp. 407-485. A particular suitable and hence preferably used carrier for the catalysts used in the present process is magadiite ($Na_2Si_{14}O_{29}.9H_2O$), since the use of this carrier results in a high content of hydrocarbons with 5-12 carbon atoms in the synthesis product. Magadiite is preferably used in combination with 0.1 up to 10% by weight of cobalt advantageously promoted with up to 10% by weight of chromium, cobalt being incorporated into the magadiite by ion-exchange and chromium by impregnation.

Another very selective catalyst is obtained by incorporating 0.1 up to 15% by weight of ruthenium into the magadiite by ion exchange.

The catalyst combinations used in the process according to the invention contain one or more metal components with catalytic activity for the conversion of an $H_2/CO$ mixture into acyclic hydrocarbons. Catalyst components capable of converting an $H_2/CO$ mixture into mainly acyclic hydrocarbons are known in the literature as Fischer-Tropsch catalysts. Such catalyst components consist of one or more metals of the iron group or ruthenium together with one or more promoters to increase the activity and/or selectivity. Per 100 parts by weight of carrier suitable catalysts contain 1-15 parts by weight of ruthenium and/or 10-75 parts by weight of one or more metals of the iron group together with one or more promoters in a quantity of 1-50% of the quantity of the iron group metals present on the catalyst.

As promoters for the catalysts according to the invention a large number of elements are suitable. The following may be mentioned as examples: alkali metals, alkaline earth metals, metals of group VIB, Ti, Zr, Al, Si, As, V, Mn, Cu, Ag, Zn, Cd, Bi, Pb, Sn, Ce, Th and U. Very suitable promoter combinations for iron catalysts according to the invention consist of an alkali metal such as K, a readily reducible metal such as Cu or Ag and optionally a metal difficult to reduce, such as Al or Zn. An example of a very suitable iron catalyst according to the invention is a catalyst containing iron, potassium and copper on a crystalline laminar silicate as carrier. If in the process according to the invention use is made of an iron catalyst containing K as selectivity promoter, a catalyst containing not more than 0.15 g of K per g of Fe is preferred, since it has been found that if higher K concentrations are applied the selectivity does not rise further while the stability substantially decreases as a result of carbon deposition of the catalyst.

Very suitable promoter combinations for cobalt catalysts according to the invention consist of an alkaline earth metal and Cr, Zr, Th, U or Ce. An example of a very suitable cobalt catalyst according to the invention is a catalyst containing cobalt, magnesium and thorium on a laminar crystalline silicate as carrier. Other very suitable cobalt catalysts according to the invention are catalysts containing Co/Cr, Co/Zr, Co/Zn or Co/Mg on a crystalline laminar silicate as carrier. Very suitable promoters for nickel catalysts according to the invention are Al, Mn, Th, W and U.

If in the process according to the invention it is intended to use a catalyst combination of which the catalyst component having Fischer-Tropsch activity is iron, an iron catalyst is preferably chosen containing a promoter combination consisting of an alkali metal, a readily reducible metal such as copper or silver and optionally a metal difficult to reduce, such as aluminum or zinc. A very suitable iron catalyst for the present purpose is a catalyst prepared by impregnation containing iron, potassium and copper on a crystalline laminar silicate as carrier. If in the catalyst combination iron is used as catalyst component having the required Fischer-Tropsch activity, the process according to the invention is preferably carried out at a temperature of 250°–375° C. and a pressure of 10–50 bar.

If in the process according to the invention it is intended to use a catalyst combination of which the catalyst component having the required Fischer-Tropsch activity is cobalt, a cobalt catalyst is preferred containing a promoter combination consisting of an alkaline earth metal and chromium, thorium, uranium or cerium.

A very suitable cobalt catalyst for the present purpose is a catalyst prepared by ion exchange and containing cobalt, magnesium and thorium on a crystalline laminar silicate as carrier. Other very suitable cobalt catalysts prepared by ion exchange are catalysts containing, in addition to cobalt, one of the elements chromium, titanium, zirconium and zinc on the silicate as carrier.

If in the catalyst combination cobalt is used as catalyst having the required Fischer-Tropsch activity, the process according to the invention is preferably carried out at a temperature of 220°–300° C. and a pressure of 10–35 bar.

Very suitable catalysts for the process according to the invention are:

(a) catalysts containing 10–75 parts by weight of iron and 5–40 parts by weight of magnesium per 100 parts by weight of crystalline laminar silicate carrier and prepared by ion-exchange of the carrier with one or more aqueous solutions of salt of iron and of magnesium followed by drying the composition, calcining it at a temperature of 200°–1200° C. and reducing it. Special preference is given to such catalysts containing, in addition to 20–60 parts by weight of iron and 7.5–30 parts by weight of magnesium, 0.5–5 parts by weight of copper as reduction promoter and 1–5 parts by weight of potassium as selectivity promoter per 100 parts by weight of carrier and calcined at 750°–850° C. and reduced at 200°–350° C.;

(b) catalysts containing 10–40 parts by weight of iron and 0.25–10 parts by weight of chromium per 100 parts by weight of crystalline laminar silicate carrier and prepared by ion exchange of the carrier with one or more aqueous solutions of salts of iron and of chromium followed by drying the composition, calcining it and reducing it at a temperature of 350°–750° C. Particular preference is given to such catalysts containing, in addition to 20–35 parts by weight of iron and 0.5–5 parts by weight of chromium, 1–5 parts by weight of potassium as selectivity promoter and calcined at 200°–700° C. and reduced at 200°–600° C.;

(c) catalysts containing 10–40 parts by weight of cobalt and 0.25–5 parts by weight of zirconium, titanium or chromium per 100 parts by weight of crystalline laminar silicate carrier and prepared by ion exchange of a silica carrier with one or more aqueous solutions of salts of cobalt and zirconium, titanium or chromium, followed by drying the composition, calcining at 200°–700° C. and reducing it at 200°–700° C.

In the process according to the invention catalysts are preferably used that are prepared by ion-exchange of the carrier with one or more aqueous solutions of salts of ruthenium or of metals of the iron group and salts of promoters, followed by drying and calcining the composition.

In the preparation of the catalysts the salts can be deposited on the carrier in one or more steps. Between the separate ion-exchange and/or impregnation steps the material is dried. For the preparation of catalysts with a high metal content the use of a multi-step technique may be necessary. The salts of the iron group metals and the salts of the promoters can be deposited on the carrier separately or together from one solution.

In the process according to the invention the intention is to convert the largest possible quantity of the CO present in the feed into acyclic hydrocarbons over a catalyst containing one or more metal components with catalytic activity for the conversion of an $H_2/CO$ mixture into acyclic hydrocarbons, which metal components are chosen from the group formed by iron, cobalt, nickel and ruthenium. To this end the $H_2/CO$ molar ratio in the feed is suitably at least 1.0 and preferably 1.25–2.25.

The process according to the invention can very suitably be carried out by conducting the feed in upward or downward direction through a vertically mounted reactor containing a fixed bed of the monofunctional catalyst or of the bifunctional catalyst combination. The process can also be carried out using a suspension of the catalyst or catalyst combination in a hydrocarbon oil. The process is preferably carried out under the following conditions: a temperature of 125°–375° C. and in particular of 175°–275° C. and a pressure of 1–150 bar and in particular of 5–100 bar.

The invention will now be explained with reference to the following examples, which are intended to be purely exemplary of the invention.

EXAMPLE 1

Magadiite was prepared according to the recipe by Lagaly et al. as described in "American Mineralogist" 60 (1975) p. 642, which is incorporated herein by reference. The magadiite obtained was first transferred into the ammonium form by ion-exchange with a concentrated $NH_4OH$ solution. The ammonium form of the magadiite was then impregnated with an aqueous solution of chromium nitrate (2.3% wt. $Cr(NO_3)_3 9H_2O$) and dried. The impregnated magadiite was ion-exchanged with an aqueous solution of $Co(NH_3)_6(NO_3)_2$ (2.1% wt.) during 24 hours. The catalyst was then dried at 110° C., calcined for two hours at 500° C. in air and subjected to a 24-hour reduction at 575° C. with hydrogen at atmospheric pressure. The resulting catalyst had the following composition: 25 Co/1 Cr/296 SiO$_2$.

A gas mixture consisting of H$_2$ and CO (H$_2$/CO=1) was passed over this catalyst applying the following conditions:

gas hourly space velocity: 1000 l (NTP)/1h
pressure: 20 bar
temperature: 260° C.

The conversion of H$_2$+CO into hydrocarbons was 71% wt.

The space-time yield was 138 grams of hydrocarbons per liter of catalyst volume per hour.

The selectivity is given in the following table:

| | |
|---|---|
| C$_1$ + C$_2$ | 22% |
| C$_3$ + C$_4$ | 10% |
| C$_5$ – C$_{12}$ | 50% |
| C$_{13}$ – C$_{19}$ | 12% |
| C$_{20}$ + | 6% |

From this table it can be seen that the yield of desired hydrocarbons boiling in the gasoline boiling range (C$_5$-C$_{12}$) is very high compared with those boiling below and above the preferred range.

EXAMPLE 2

The ammonium form of magadiite was prepared as shown in Example 1. It was ion-exchanged with a solution of ruthenium chloride, dried and calcined for 2 hours at 500° C. in air at atmospheric pressure and reduced for two hours at 280° C. with hydrogen and nitrogen (molar ratio 3/1) at atmospheric pressure in order to obtain a catalyst having the composition: 1 Ru/25SiO$_2$. Using this catalyst under the conditions described in Example 1 hydrocarbons were formed from a H$_2$/CO gas mixture (H$_2$/CO=1).

The space-time yield was 82 grams of hydrocarbons per liter of catalyst per hour.

The selectivity was:

| | |
|---|---|
| C$_1$ + C$_2$ | 3.7% |
| C$_3$ + C$_4$ | 5.6% |

-continued

| | |
|---|---|
| C$_5$ – C$_{12}$ | 90.6% |
| C$_{13}$ – C$_{19}$ } | |
| C$_{20}$ + | 0.1% |

An excellent result as regards the yield of gasoline components (C$_5$-C$_{12}$) was thus obtained.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A process for the preparation of a hydrocarbon mixture consisting substantially of C$_5$-C$_{12}$ hydrocarbons from a mixture of hydrogen and carbon monoxide, which comprises contacting said H$_2$/CO mixture under suitable reaction conditions with a catalyst combination containing one or more metal components with catalytic activity for the conversion of an H$_2$/CO mixture into acyclic hydrocarbons and as a carrier, magadiite, a laminar crystalline silicate compound capable of absorbing metal ions or metal salts by intercalation.

2. A process as in claim 1, wherein the reaction is carried out at a temperature of 125°-375° C. and a pressure of 1-50 bar.

3. A process as in claim 1 wherein the catalyst contains iron, nickel, cobalt, chromium and/or ruthenium.

4. A process as in claim 1 wherein the catalyst is obtained by depositing one or more metals with catalytic activity for the conversion of an H$_2$/CO mixture into acyclic hydrocarbons on the laminar crystalline silicate by ion-exchange.

5. A process as in claim 1 wherein the catalyst consists of magadiite on which 1 up to 10% by weight of cobalt is deposited by ion exchange promoted with up to 10% by weight of chromium by means of impregnation.

6. A process as in claim 1 wherein the catalyst consists of magadiite on which 0.1 up to 15% by weight of ruthenium is deposited by means of ion-exchange.

* * * * *